United States Patent [19]

Van Dyke

[11] Patent Number: 5,025,020

[45] Date of Patent: Jun. 18, 1991

[54] USE OF TETRANDRINE AND ITS DERIVATIVES TO TREAT MALARIA

[75] Inventor: Knox Van Dyke, Morgantown, W. Va.

[73] Assignee: Cancer Biologics of America, Inc., Lexington, Ky.

[21] Appl. No.: 413,711

[22] Filed: Sep. 28, 1989

[51] Int. Cl.$^5$ .............................................. A61K 31/44
[52] U.S. Cl. ................................... 514/280; 514/281; 514/895
[58] Field of Search ........................ 514/895, 280, 281

[56] References Cited

FOREIGN PATENT DOCUMENTS 4101413  1/1978  Japan .

OTHER PUBLICATIONS

Kawashima et al., Gen. Pharmac., vol. 21 #3, pp. 343-347.
Fang et al., Jour. of Hypertension, 1986, 4(Suppl 6)s-150-152.
Qian et al., Hypotensive Activity of Tetrandrine in Rats, Pharmacology 26: pp. 187-197, 1983.
Gralla et al., Toxicology Studies with d-Tetrandrine, Cancer Chemotherapy Reports Part 3, vol. 5 #1, 1974, pp. 79-85.
Dept. of Pharmacology et al., A Clinical Study of Antihypertensive Effect of Tetrandrine, Chinese Medical Jour. 92(3), pp. 193-198, 1979.
Martin et al., Science, Feb. 20, 1987, pp. 899-901.
Potentiation of Antitumor Activity of Vincristine by the Biscoclaurine Alkaloid Cepharanthine, Kato et al., JNCI, vol. 79(3), Sep. 1987, pp. 527-532.
Biochemical Effects of d-Tetrandrine and Thalacarpine, Creasey, 1976, Biochemical Pharmacology, vol. 25, pp. 1887-1891.
Cepharanthine and Multidrug Resistance, Shiraishi et al., 1987, Cancer Research 47, 2413-2416.
Reversal of Cloroquine Resistance In Falciparum Malaria Independent of Calcium Channels, Ye et al., 1988, Biochemical & Biophysical Res. Com., 155(1), pp. 476-481.
Mitscher et al., CA75: 59822w, 1971.
Miana et al., CA 72:55716e, 1970.

*Primary Examiner*—Stanley J. Friedman
*Assistant Examiner*—Russell Travers
*Attorney, Agent, or Firm*—Price, Heneveld, Cooper, DeWitt & Litton

[57] ABSTRACT

The specification discloses the treatment of malaria through the use of tetrandrine and its derivatives.

5 Claims, 1 Drawing Sheet

USE OF TETRANDRINE AND ITS DERIVATIVES TO TREAT MALARIA

CROSS REFERENCE IN RELATED APPLICATION

This application is based on the inhibitory activity of tetrandrine and all of its derivatives, specifically against malaria, as well as the ability of such derivatives, some in particular, to potentiate the effectiveness of antimalarial drugs against multidrug resistant malarial cells in particular. A related application filed concurrently herewith discloses and claims the generic ability of methoxadiantifoline, tetrandrine and certain of its derivatives to potentiate the inhibitory action of primary drugs against multidrug resistant cells generically, and to apparently reverse the normal pump out action of P-glycoprotein in such cells.

BACKGROUND OF THE INVENTION

A number of diverse drugs have been found effective against malaria. However in many cases, the initial success of physicians in treating this disease is followed by total failure. Drugs which worked initially become totally ineffective after a period of time. An initial period of remission is often followed by a period of frustration during which nothing seems to be effective against the disease. Death becomes inevitable.

Such a phenomenon is often referred to as multidrug resistance. A material cell which initially responds to treatment by one or more drugs becomes resistant to treatment by not only the drug previously used, but but any malarial treatment drug. Martin, Odula and Milhous disclosed the treatment of such multidrug resistance in malaria by using verapamil. "Reversal of Chloroquine Resistance in Plasmodium falciparaum by Verapamil," Martin et al, Science, Feb. 28, 1987. Martin et al, reports that Verapamil did reverse chloroquine resistance in malaria cells, but that the verapamil alone had no effect on the malaria.

The structural formula of verapamil is shown below:

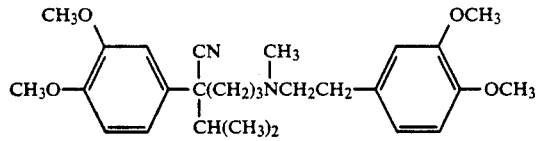

The problem with this approach is that verapamil is a calcium channel blocker. While calcium channel blockers are therapeutic in the treatment of hypertension at moderate levels, they are toxic at levels high enough to effect MDR reversal.

Consequently, researchers throughout the world continue to press for techniques for reversing multidrug resistance. A successful clinical technique for reversing multidrug resistance in malaria will be one of the most important breakthroughs in the fight against malaria.

SUMMARY OF THE INVENTION

In the present invention, it has been surprisingly found that tetrandrine and its derivatives act in reverse multidrug resistance in malaria and do not show an affinity for calcium channel blocking. Thus the toxicity problems associated with verapamil and its derivatives are avoided.

Perhaps even more surprisingly, it has been found that tetrandrine and its derivatives are also specifically effective against malaria, including multidrug resistant strains, even in the absence of primary treatment drugs. Indeed, the most surprising of all is that the most preferred tetrandrine type structure is actually more effective against multidrug resistant malarial strains than it is against drug sensitive strains.

These surprising and unexpected results, as well as other objects, advantages and features of the present invention will be more fully understood and appreciated by reference to the Description of the Preferred Embodiment and appended drawings.

DESCRIPTION OF THE PREFERRED EMBODIMENT

Figure 1:
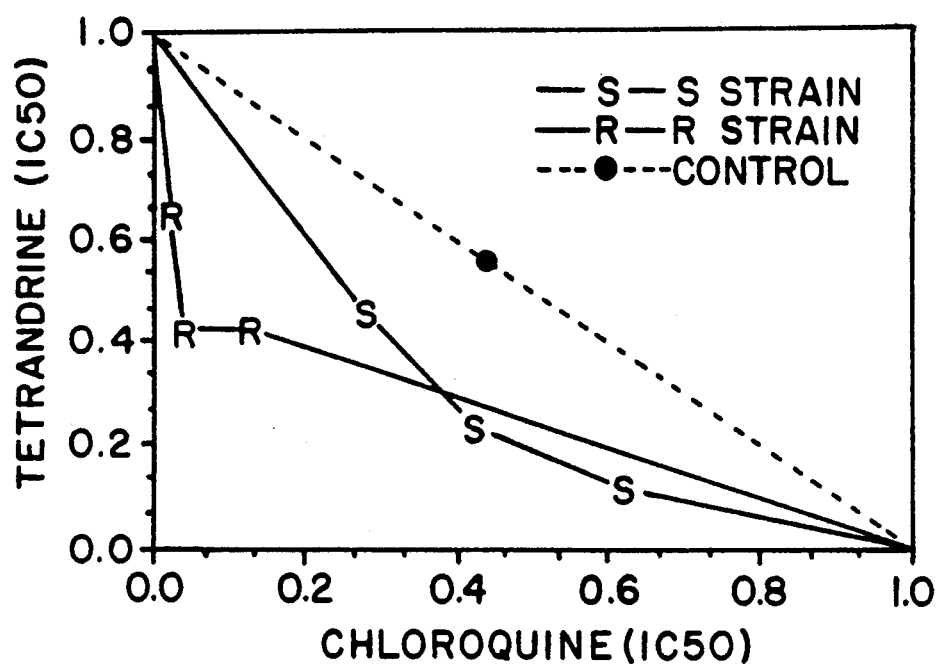
FIG. 1 is an isobologram showing the effectiveness of tetrandrine and chloroquine at 50% inhibition concentrations against sensitive and resistant malarial strains.

In the preferred embodiment, the compounds of the present invention have the following structural formula:

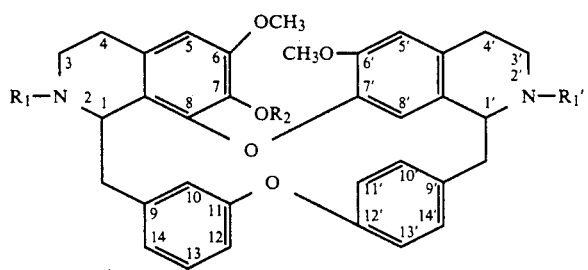

where $R_2$ and $R_1'$ are the same or different shortchained carbon based ligand including, without limitation, $CH_3$, $CO_2CH_3$, or H; and $R_2$ and $R_3$ are the same or different $CH_3$ or Hydrogen.

This family of compounds includes tetrandrine, isotetrandrine, hernandezine, barbamine, pycnamine, phaeanthine, obamegine, and fangchinoline, which list is not intended to be exhaustive. In all of these examples, $R_1$ and $R_1'$ constitute the methyl group. Variation within the group occurs in that $R_2$ and $R_3$ may constitute either a methyl group or hydrogen and the isomeric configuration of the compounds at the C-1 and C-1' chiral carbon positions is either R (rectus) or S (sinister). The rules for R and S configuration can be found in Morrison and Boyd, "Organic Chemistry," 4th Edition, Copyright 1983 by Allyn and Bacon, at pages 138-141. In addition, hernandezine includes a methoxy group at the C-5 position, a substitution which does not appear to be significant in the operability of the compound in the present invention. The specific manner in which these exemplary family members vary is set forth in Table V below, wherein these family members are compared to two non-family members for activity against drug sensitive and drug resistant strains of P. falciparum, malaria.

A specific in vivo dosage for each of the various members of the tetrandrine family for reversing malarial multidrug resistence and/or for specifically treating malaria has not been established. However, such dosage can be established through routing clinical experimentation by referencing the concentrations at which the various compounds have exhibited 50% inhibition as set forth Tables I through V herein. These concentrations have been from about 0.1 to about 3 micro molar. Such concentrations can be achieved in vivo by administering dosages of from about 100 to about 300 mg/day. It is known that at these concentrations, tetrandrine is substantially non-toxic. The preferred method for administering the drug is orally, though other methods such as injection may be used.

Prior studies of tetrandrine for various other uses have indicated a minimal toxicity at doses of from 100 to 300 mg/day. Tetrandrine and several tetrandrine derivatives were screened for calcium channel blocker activity, and such was found to be minimal. Thus, the toxicity problems associated with higher doses of calcium channel blockers such as verapamil are not observed in members of the tetrandrine family.

The effectiveness of tetrandrine in reversing malarial multidrug resistance was determined by comparing the antimalarial action of tetrandrine and chloroquine alone and in combination against a *P. falciparum* malarial strain which is sensitive to chloroquine and another which is resistant to chloroquine. A similar study was conducted using tetrandrine and qinghaosu. Chloroquine and Qinghaosu are commonly used antimalaria drugs.

The dose ($IC_{50}$) of each drug or each drug combination required to effect a 50% inhibition in the malarial activity of each strain was determined by establishing a dose response curve for each.

FCMSU1/Sudan strain and cloned inochine (W-2) strain of *P. falciparum* were used. The former is sensitive to chloroquine and the latter is resistant to chloroquine. The two strains of the parasite were cultured according to the candle jar method of Trager and Jensen, Science 193,673–675, 1976. In a given experiment, 4-day-old Petri dish cultures (approx. 10% parasitemai) were diluted with medium containing an amount of noninfected type A human erythrocytes to obtain a culture with a final hematocrit of 1.5% and parasitemia of 0.5–1.0%. The resulting culture was ready for addition to microtitration plates with 96 flat-bottom wells.

The testing procedure used was similar to that described by Desjardins et al, in Antimicrobial Agents and Chemotherapy, 16, 710–718 (1979). Briefly, the final volume added to each of the 96-well micrtitration plates was 250 μl and consisted of 15μl of complete medium with or without the primary drug (chloroquine or qinghaosu, 175 μl or either the parasitized culture or a nonparasitized human erythrocyte control, and 25 μl or complete medium with or without tetrandrine. 25 μl radio active (0.5 μCl) [2,8-$^3$H] adenosine. The microtitration plates were incubated in a candle jar for an additional 28 hr, at 37° C.

As the malaria parasite grows $^3$H-adenosine is metabolized and incorporates into polymeric RNA and DNA. The labeled polymers are trapped on glass fiber filters and unincorporated material is washed away. In the absence of drug there is 100% incorporation of the labeled material. When drugs interfere (directly or indirectly), an inhibitory dose of 50% ($IC_{50}$) can be calculated. The experiments were repeated three times except where noted. Statistical analysis was done using Student's t test for significance. VanDyke et al, "Exp Parasitol," Vol 64, 418–423 (1967).

Figure 2:
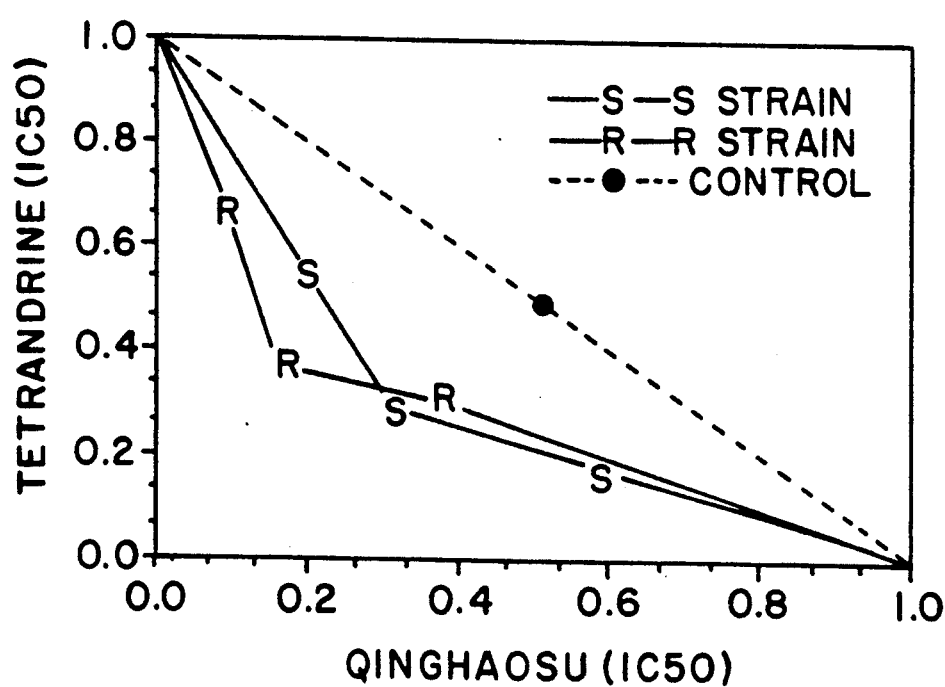
FIG. 2 is an isobologram showing the effectiveness of tetrandrine and qinghaosu at 50% inhibition concentrations against sensitive and resistant malarial strain.

Tetrandrine completely reversed resistance in chloroquine in chloroquine-resistant malaria. When tetrandrine is added to Chloroquine, it supplements and potentiates the antimalarial activity. When tetrandrine is added to Qinghaosu, it provides long-acting and synergistic activity to Qinghaosu. This can be seen if Tables I, II, III, and IV while isobolograms (FIGS. 1 and 2) of Tetrandrine and Chloroquine as well as Tetrandrine and Qinghaosu reveal the synergistic and potentiating activity of Tetrandrine when added to Chloroquine or Qinghaosu. Remarkable, when 3.0μMolar Tetrandrine is added to 0.1μMolar Chloroquine, the $IC_{50}$ of Chloroquine can be lowered 43- Fold.

TABLE 1

$IC_{50}$ (nM) OF TT AND CQ FOR EACH DRUG ALONE AND IN COMBINATION*

| MALARIA*** | SINGLE DRUG | | DRUG COMBINATION** | | |
|---|---|---|---|---|---|
| | TT | CQ· | TT (1.0 uM) CQ (0.3 uM) | TT (2.0 uM) CQ (0.2 uM) | TT (3.0 uM) CQ (0.1 uM) |
| S STRAIN | 498.1 ± 93.7 | 26.7 ± 3.8 | 54.9 ± 7.1 (TT) | 114.1 ± 23.0 (TT) | 223.3 ± 38.6 (TT) |
| | | | 16.5 ± 2.1 (CQ) | 11.4 ± 2.3 (CQ) | 7.4 ± 1.3 (CQ) |
| R STRAIN | 197.5 ± 24.7 | 185.8 ± 4.9 | 79.5 ± 13.7 (TT) | 79.5 ± 16.1 (TT) | 124.6 ± 9.6 (TT) |
| | | | 23.8 ± 4.1 (CQ) | 8.0 ± 1.6 (CQ) | 4.2 ± 0.3 (CQ) |

*The data in the table above are the mean values ± S.D. (nM) from three experiments except where noted.
**Ratios of TT/CQ in the drug combinations are 10:3, 10:1 and 30:1 respectively.
***S and R strains represent CQ-sensitive (FCMSU1/Sudan) and resistant (w2) strain of *P. falciparum* respectively.

When the inhibiting activity of two drugs e.g. and B are compared, the middle point of the dose response curve is usually chosen as the basis for comparison. This point is known as the inhibitory dose that occurs at the point of 50% inhibition of the response to be measured (inhibitory concentration at 50% inhibitory response=$IC_{50}$.) An isobologram is developed by comparing the $IC_{50}$ or one drug against the other i.e. drug A against Drug B. We start by putting the $IC_{50}$ of Drug B at the top of the y axis marked I.O. The $IC_{50}$ of Drug A is placed at the position 1.0 on the x axis. The combinations of Drug A and Drug B are mixed and tested that are below $IC_{50}$ of either drug and the points are located on the graph. If the two drugs are additive there is a straight line between the $Y_1X_0$ (Drug B) and $Y_0X_1$ (Drug A). If the line or curve bends below the straight line the drugs are synergistic or potentiating. If the line bends above the straight line the two drugs are antagonistic.

TABLE 2

IC$_{50}$ (nM) OF TT AND QHS FOR EACH DRUG ALONE AND IN COMBINATION*

| MALARIA*** | SINGLE DRUG | | DRUG COMBINATION** | | |
|---|---|---|---|---|---|
| | TT | QHS | TT (1.0 uM) QHS (0.3 uM) | TT (2.0 uM) QHS (0.2 uM) | TT (3.0 uM) QHS (0.1 uM) |
| S STRAIN | 410.2 ± 69.0 | 36.7 ± 4.7 | 71.9 ± 8.9 (TT) 21.6 ± 2.7 (QHS) | 113.5 ± 6.3 (TT) 11.4 ± 0.6 (QHS) | 219.5 ± 35.5 (TT) 7.3 ± 1.2 (QHS) |
| R STRAIN | 205.6 ± 49.8 | 47.8 ± 14.5 | 59.6 ± 13.7 (TT) 17.9 ± 4.1 (QHS) | 71.8 ± 13.8 (TT) 7.2 ± 1.4 (QHS) | 136.9 ± 41.6 (TT) 4.6 ± 1.4 (QHS) |

*The data in the table above are the mean values ± S.D. (nM) from three experiments except where noted.
**Ratios of TT/QHS in the drug combinations are 10:3, 10:1 and 30:1 respectively.
***S and R strains represent CQ-sensitive (FCMSU1/Sudan) and resistant (W2) strain of *P. falciparum* respectively.

TABLE 3

EFFECT OF COMBINATION OF TETRANDRINE AND CHLORQUINE ON *P. FALCIPARUM*

| MALARIA** | TRIAL | SFIC* | | |
|---|---|---|---|---|
| | | 1.0 uM TT 0.3 uM CQ | 2.0 uM TT 0.2 uM CQ | 3.0 uM TT 0.1 uM CQ |
| S STRAIN | 1 | 0.77 | 0.66 | 0.73 |
| | 2 | 0.64 | 0.77 | 0.70 |
| | 3 | 0.78 | 0.55 | 0.75 |
| | MEAN ± S.D. | 0.73 ± 0.06 | 0.66 ± 0.09 | 0.73 ± 0.02 |
| R STRAIN | 1 | 0.60 | 0.45 | 0.74 |
| | 2 | 0.68 | 0.63 | 0.76 |
| | 3 | 0.36 | 0.30 | 0.50 |
| | MEAN ± S.D. | 0.55 ± 0.14 | 0.46 ± 0.14 | 0.67 ± 0.12 |

*SFIC represents sum of fractional inhibitory concentration as described by Berenbaum (11), SFIC is equal to one in cases of additive effects of the drugs, higher than one in cases of antagonism and lower than one in synergistic action.
**S and R strain: chloroquine sensitive (FCMSU1/Sudan) and resistant (W2) strain of *P. falciparum*.

TABLE 4

EFFECT OF COMBINATION OF TETRANDRINE AND QINGHAOSU ON *P. FALCIPARUM*

| MALARIA** | TRIAL | SFIC* | | |
|---|---|---|---|---|
| | | 1.0 uM TT 0.3 uM QHS | 2.0 uM TT 0.2 uM QHS | 3.0 uM TT 0.1 uM QHS |
| S STRAIN | 1 | 0.77 | 0.68 | 0.71 |
| | 2 | 0.74 | 0.49 | 0.72 |
| | 3 | 0.79 | 0.62 | 0.77 |
| | MEAN ± S.D. | 0.77 ± 0.02 | 0.60 ± 0.08 | 0.73 ± 0.03 |
| R STRAIN | 1 | 0.63 | 0.46 | 0.71 |
| | 2 | 0.77 | 0.72 | 0.74 |
| | 3 | 0.64 | 0.40 | 0.81 |
| | MEAN ± S.D. | 0.68 ± 0.06 | 0.52 ± 0.14 | 0.75 ± 0.04 |

*SFIC represents sum of fractional inhibitory concentration as described by Berenbaum (11), SFIC is equal to one in cases of additive effects of the drugs, higher than one in cases of antagonism and lower than one in synergistic action.
**S and R strain: chloroquine sensitive (FCMSU1/Sudan) and resistant (w2) strain of *P. falciparum*.

Tetrandrine and various of its derivatives were also compared to non-tetrandrine derivatives for their effectiveness against a chloroquine sensitive and a chloroquine resistant strain of *P. falciparum* malaria. The test procedure was basically the same as outlined above. The non family members were cycleanine and capharanthine, whose structural formulas are illustrated below:

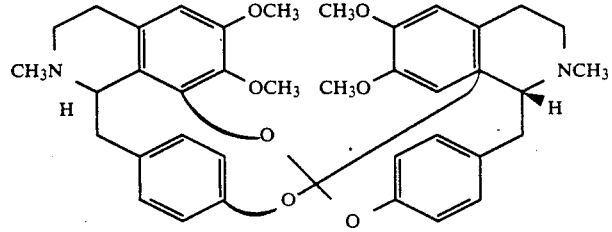

Structure of cycleanine

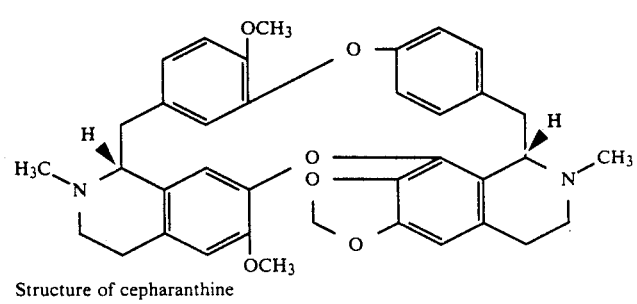

Structure of cepharanthine

These comparative activities are set forth in Table V below.

TABLE V

**CHEMICAL STRUCTURE-ANTIMALARIAL ACTIVITY OF BISBENZYLISO-QUINOLINE ALKALOIDS AGAINST *PLASMODIUM FALCIPARUM* IN VITRO**

| Drug | Configuration | | Substituents | | | | Oxygen | $IC_{50}$ $(10^{-7}$ M) | | Ratio |
|------|---------------|------|------|------|------|------|--------|------|------|-------|
| (a) | C-1 | C-1' | C-5 | C-7 | C-12 | C-5' | Bridge | S** | R** | (S/R)* |
| TT | S | S | H | OCH3 | OCH3 | | C8–C7° C11–C12° | 2.9 | 1.2 | 2.6 |
| IT | R | S | H | OCH3 | OCH3 | | C8–C7° C11–C12° | 4.8 | 1.4 | 3.5 |
| HE | S | S | OCH3 | OCH3 | OCH3 | | C8–C7° C11–C12° | 3.7 | 1.3 | 2.8 |
| BB | R | S | H | OCH3 | OH | | C8–C7° C11–C12° | 4.6 | 1.9 | 2.7 |
| PY | R | R | H | OCH3 | OH | | C8–C7° C11–C12° | 3.8 | 4.2 | 0.9 |
| PH | R | R | H | OCH3 | OCH3 | | C8–C7° C11–C12° | 6.0 | 5.0 | 1.2 |
| OB | R | S | H | OH | OH | | C8–C7° C11–C12° | 6.6 | 4.8 | 1.5 |
| FA | S | S | H | OH | OCH3 | | C8–C7° C11–C12° | 2.6 | 2.2 | 1.2 |
| CY | R | R | H | OCH3 | | | C8–C12° C12–C8° | 32 | 42 | 0.8 |
| CE | S | R | H | OCH2-(ring) | | | C8–C7° C12–C11° | 10 | 9.4 | 1.1 |

(a) TT — tetrandrine; IT — isotetrandrine; HE — hernandezine; BB — berbamine; PY — pycnamine; PH — phaeanthine; OB — obamegine; FA — fangchinoline; CY — cycleanine; CE — cepharanthine.
*$IC_{50}$ of a drug against sensitive strain of *P. falciparum* is devided by $IC_{50}$ for resistant strain.
**S and R represent chloroquine-sensitive and resistant strain of *P. falciparum*.

The results of table V show that tetrandrine and its derivatives are far more effective against either the chloroquine sensitive material strain or the chloroquine resistant strain than are either cycleanine or cepharanthine. Cepharanthine was the better of the non family compounds, and $9.4 \times 10^{-7}$ moles were required to effect a 50% inhibition in activity in the resistant strain, as compared to $5 \times 10^{-7}$ moles of phaeanthine, the least effective member of the tetrandrine family. The performance of cycleanine was much worse, requiring 3 to 4 times the quantity of cepharanthine to effect 50% inhibition.

The results of Table V also illustrate that those members of the tetrandrine family having the "S" isomeric configuration at the C-1 chiral carbon and having at least one of the $R_2$ and $R_3$ substituants comprising $CH_3$ are the most effective members of the family against the chloroquine resistant malarial strains. Further where $R_2$ specifically constitutes a $CH_3$ substituant, the tetrandrine family member is actually substantially more effective against the chloroquine resistant malarial strain than it is against the chloroquine sensitive malarial strain. This extremely surprising result suggests that these family members would also be the most effective members of the family in effecting multidrug resistance reversal. Thus, the preferred tetrandrine family members have the "S" configuration at the C-1' carbon location and have at least one of $R_2$ and $R_3$ comprising $CH_3$, and most preferably with at least $R_2$ comprising $CH_3$.

Of course it is understood that the above is merely a preferred embodiment of the invention and that various changes and alterations can be made without departing from the spirit and the broader aspects thereof.

I claim:

1. A method for treating malaria comprising: exposing malaria cells to effective concentrations of a compound having the following formula:

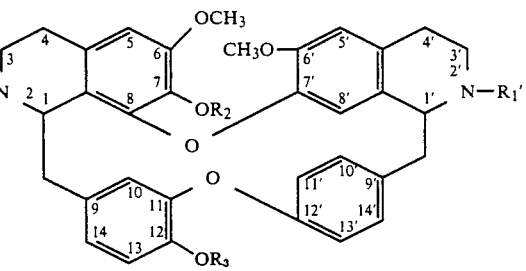

where $R_1$ and $R_1'$ are the same or different shortchained carbon based ligand; and $R_2$ and $R_3$ are the same or different $CH_3$ or hydrogen.

2. The method of claim 1 where: the isomeric configuration of the C-1' chiral carbon location is "S" and at least one of $R_2$ and $R_3$ comprises $CH_3$.

3. The method of claim 2 where: $R_2$ comprises $CH_3$.

4. The method of claim 3 in which said compound comprises tetrandrine.

5. The method of claim 4 in which said compound is used at dosage level of from about 100 to about 300 mg per day.

* * * * *